(12) United States Patent
Yamaura et al.

(10) Patent No.: US 8,677,998 B2
(45) Date of Patent: Mar. 25, 2014

(54) OXYGEN CONCENTRATOR

(75) Inventors: Yuki Yamaura, Yamaguchi (JP); Hisashi Kiriake, Yamaguchi (JP)

(73) Assignee: Teijin Pharma Limited, Tokyo (JP)

( * ) Notice: Subject to any disclaimer, the term of this patent is extended or adjusted under 35 U.S.C. 154(b) by 31 days.

(21) Appl. No.: 13/521,393

(22) PCT Filed: Jan. 7, 2011

(86) PCT No.: PCT/JP2011/050593
§ 371 (c)(1),
(2), (4) Date: Jul. 10, 2012

(87) PCT Pub. No.: WO2011/087111
PCT Pub. Date: Jul. 21, 2011

(65) Prior Publication Data
US 2012/0291884 A1   Nov. 22, 2012

(30) Foreign Application Priority Data
Jan. 12, 2010   (JP) .................................. 2010-003911

(51) Int. Cl.
*A61M 16/00*   (2006.01)
(52) U.S. Cl.
USPC ............. 128/204.21; 128/205.24; 251/129.04
(58) Field of Classification Search
USPC .......................... 128/204.18, 204.21, 205.24; 251/129.04
See application file for complete search history.

(56) References Cited

U.S. PATENT DOCUMENTS

| | | | | |
|---|---|---|---|---|
| 5,813,655 | A * | 9/1998 | Pinchott et al. ........... | 251/129.04 |
| 6,470,885 | B1 * | 10/2002 | Blue et al. ................ | 128/204.18 |
| 7,225,809 | B1 * | 6/2007 | Bowen et al. ............. | 128/204.21 |
| 7,331,343 | B2 * | 2/2008 | Schmidt et al. ........... | 128/205.24 |
| 7,552,731 | B2 * | 6/2009 | Jorczak et al. ............ | 128/205.24 |
| 2007/0209662 | A1 * | 9/2007 | Bowen et al. ............. | 128/204.21 |
| 2010/0078017 | A1 * | 4/2010 | Andrieux et al. ........ | 128/202.22 |

FOREIGN PATENT DOCUMENTS

| | | |
|---|---|---|
| JO | 2005-231443 A | 9/2005 |
| JP | H04-197268 A | 7/1992 |
| JP | 2008-136663 A | 6/2008 |
| JP | 2008-137853 A | 6/2008 |

OTHER PUBLICATIONS

Search Report in international application No. PCT/JP2011/050593, dated Mar. 1, 2011.

* cited by examiner

*Primary Examiner* — John Bastianelli
(74) *Attorney, Agent, or Firm* — Rader, Fishman & Grauer PLLC

(57) ABSTRACT

The present invention provides an oxygen concentrator which allows the flow rate setting to be changed safely and securely by the patient using a remote control device, the oxygen concentrator comprising a control means which does not allow the operation of the flow rate setting change button unless the remote control device receives the information on the flow rate setting value of the oxygen-enriched gas supplied by the current oxygen concentrator main body.

6 Claims, 5 Drawing Sheets

OXYGEN CONCENTRATOR

FIELD OF THE INVENTION

The present invention relates to a pressure swing adsorption type oxygen concentrator containing an adsorbent which preferentially adsorbs nitrogen over oxygen, more particularly to an oxygen concentrator in which the flow rate of the oxygen-enriched gas generated can be set by remote control operation.

BACKGROUND ART

In recent years, an increasing number of patients are suffering from respiratory diseases such as asthma, pulmonary emphysema, chronic bronchitis, etc. One of the most effective therapies for these diseases is oxygen inhalation therapy. In such oxygen inhalation therapy, oxygen gas or oxygen-enriched gas is inhaled by the patient. An oxygen concentrator, liquid oxygen, an oxygen gas cylinder, etc. are known as the oxygen source, among which the oxygen concentrator is mainly used for home oxygen therapy due to its convenience in using and easiness in maintenance.

The oxygen concentrator separates, concentrates and supplies oxygen which exists in air in about 21%. The oxygen concentrator includes a membrane type oxygen concentrator in which a selective oxygen permeable membrane is used and a pressure swing adsorption type oxygen concentrator containing an adsorbent which preferentially adsorbs nitrogen or oxygen. The latter is mainly used because as high concentration as 90% or more of oxygen is obtained.

The pressure swing adsorption type oxygen concentrator can generate highly concentrated oxygen-enriched gas continuously by alternately repeating a pressurization/adsorption step in which nitrogen is adsorbed to an adsorbent and unadsorbed oxygen is obtained under a pressurized condition by supplying air compressed with a compressor to the adsorbent column filled with molecular sieve zeolite such as 5A type, 13X type, Li—X type, etc. as the adsorbent which preferentially adsorbs nitrogen over oxygen and a depressurization/desorption step in which the adsorbent is regenerated by reducing the pressure in the adsorbent column to atmospheric pressure or less, purging nitrogen adsorbed to the adsorbent.

In such an oxygen concentrator, the man-machine user interface such as an operation start/stop switch and oxygen flow rate setting switch is integrated in the main body in order to supply oxygen as prescribed by the physician.

CITATION LIST

Patent Documents

Patent Document 1: Japanese Patent Application Laid-Open Publication No. H4-197268
Patent Document 2: Japanese Patent Application Laid-Open Publication No. 2008-136663

SUMMARY OF THE INVENTION

Problems to be Solved by the Invention

Regarding the oxygen concentrator, Japanese Patent Application Laid-Open Publication No. H4-197268 teaches a technique that switching on and off of the oxygen concentrator may be achieved by remote control operation. For a serious respiratory disease patients to whom as high as 5 L or more of oxygen supply flow per minute is prescribed, there is a strong requirement that the flow rate setting be changed at hand in order to increase the oxygen supply flow rate beforehand, because temporary oxygen shortage occurs upon transferring from resting mode to exerting mode. On the other hand, requirement for switching on and off of the apparatus by remote control is not so demanding.

Japanese Patent Application Laid-Open Publication No. 2008-136663 discloses a wired or a wireless remote control by which the flow rate setting may be changed as a means to solve these requirements. However, the wire should be laid along the cannula in the case of the wired remote control and such a wired remote control may not be used if the cannula is extended for use. In addition, entanglement of the cannula and the wire may cause another problem.

These problems may be solved by using the wireless remote control. However, the technique disclosed in Patent Document 2 is not sufficient for the safety measures, because the patient can neither confirm the current flow rate setting, nor be aware of the situation when a communication error occurs during operation of the remote control.

Means to Solve the Problems

The present inventor has reached the following invention to solve these problems. That is, the present invention provides an oxygen concentrator which allows the flow rate setting value of the oxygen-enriched gas to be changed by remote control operation, comprising an oxygen concentrator main body provided with a flow rate setting means to separate oxygen in air and supply the oxygen-enriched gas generated at a predetermined flow rate and a remote control device to control the oxygen concentrator main body from a distance, the oxygen concentrator main body comprising a bidirectional communication means A to transmit and receive the information on the flow rate setting value to and from the remote control device and a control means A to confirm the information and control the flow rate setting, the remote control device comprising a confirmation button to confirm the flow rate setting value of the oxygen-enriched gas currently supplied by the oxygen concentrator main body, a flow rate setting change button to change the flow rate setting value of the oxygen-enriched gas supplied by the oxygen concentrator main body, a display to indicate the flow rate setting value, and a bidirectional communication means B to transmit and receive the information on the flow rate setting value to and from the oxygen concentrator main body, and the remote control device further comprising a control means B which does not allow the operation of the flow rate setting change button unless the remote control device receives the information on the flow rate setting value of the oxygen-enriched gas supplied by the current oxygen concentrator main body.

Furthermore, the present invention provides an oxygen concentrator wherein the flow rate setting change button of the remote control device is a button to change the flow rate setting value in a stepwise fashion and the control means B is a means to transmit the flow rate setting information after a change of the first stage to the oxygen concentrator main body and to control so that the operation of the flow rate setting change button to change the flow rate to the next stage is not allowed unless the remote control device receives the information on the flow rate setting value of the oxygen-enriched gas supplied by the oxygen concentrator main body after the change.

Furthermore, the present invention provides an oxygen concentrator wherein the oxygen concentrator main body and the remote control device are each provided with individual ID, the remote control device transmitting its ID to the oxygen concentrator main body when the confirmation button is pressed, the oxygen concentrator main body returning the information on the flow rate setting value of the oxygen-enriched gas supplied by the current oxygen concentrator main body if the ID information received and the ID of the oxygen concentrator main body coincide and transmitting an error message if the IDs do not coincide, the remote control device having a display function to indicate the error message at the display and a buzzer to sound an alarm when an error has occurred in the communication between the remote control device and the oxygen concentrator main body, and the communication means between the remote control device and the oxygen concentrator main body being a bidirectional communication means based on the infrared data communication.

Furthermore, the present invention provides an oxygen concentrator wherein the flow rate setting change button of the remote control device is disposed on a surface lower than the housing surface of the remote control device, so that the button surface is located lower than the housing surface, and is provided with a cover to prevent operational error.

Advantage of the Invention

According to the present invention, the flow rate of the oxygen-enriched gas generated by the oxygen concentrator main body can be changed by remote control operation using a remote control device and the difference between the target flow rate value and an actual supply flow rate caused by the communication error can be secured to the minimum by performing stepwise change of the flow rate based on the current flow rate setting value of the oxygen concentrator main body. Furthermore, the patient can be aware of the error occurrence in the communication between the remote control device and the main body and can try again the communication. Therefore, a safer and more convenient oxygen concentrator can be provided.

DESCRIPTION OF THE EMBODIMENTS

Figure 1:
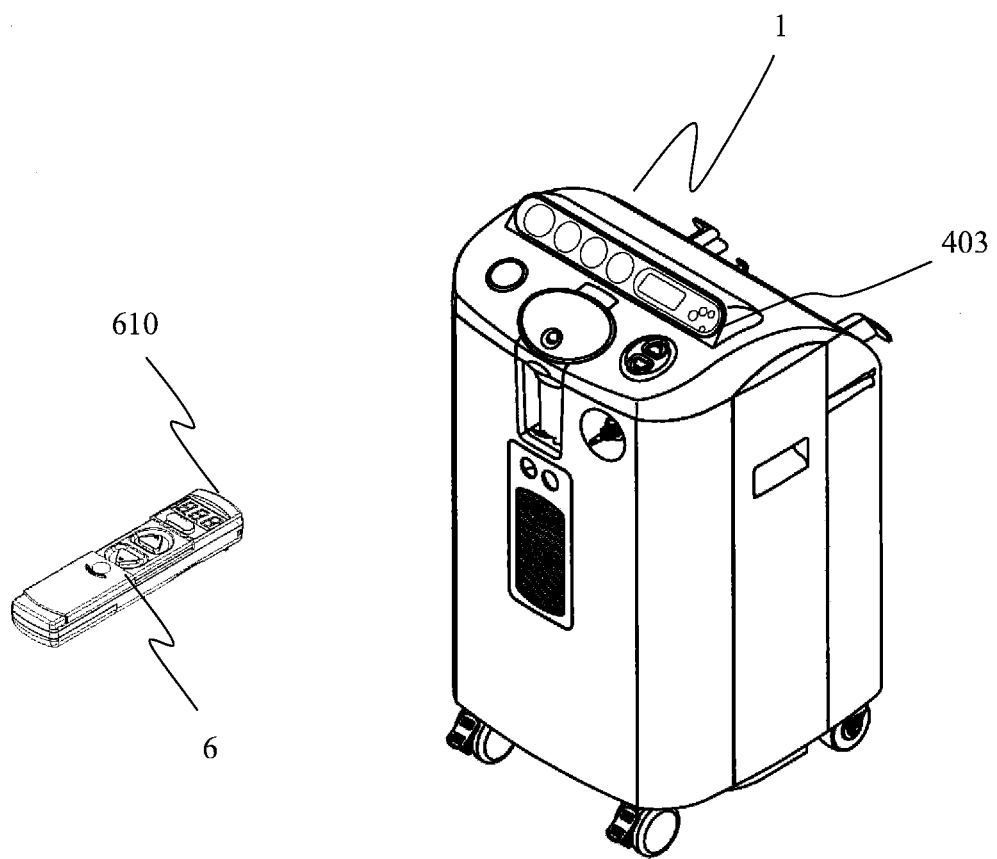
FIG. 1 is an external view of the pressure swing adsorption type oxygen concentrator as an embodiment of the oxygen concentrator of the present invention.
Figure 2:
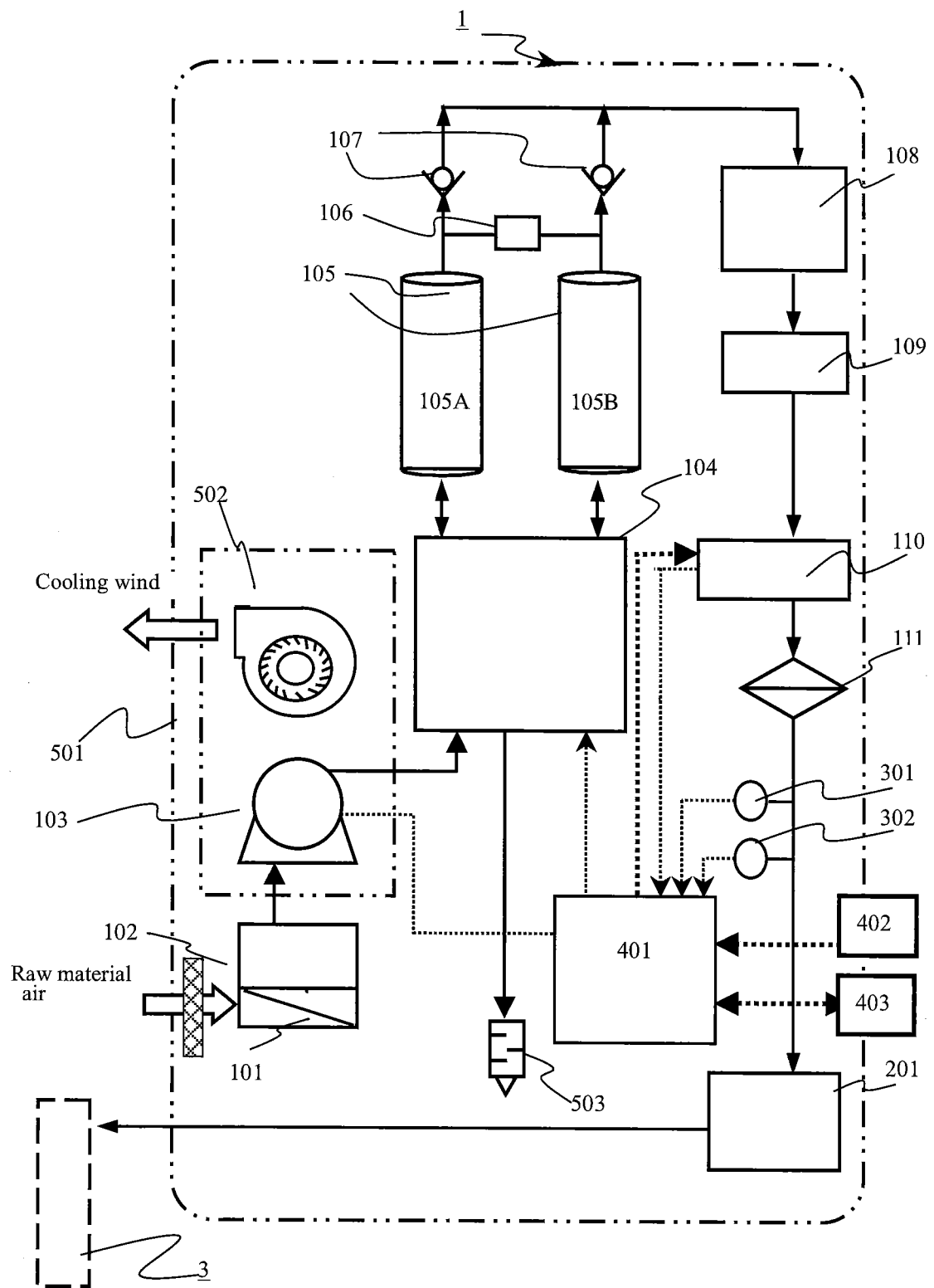
FIG. 2 is a schematic diagram of the oxygen concentrator main body.

The embodiments of the oxygen concentrator of the present invention will be described referring to the drawings.
FIG. 1 is an external view of the pressure swing adsorption type oxygen concentrator as an embodiment of the present invention. FIG. 2 is a schematic configuration of the oxygen concentrator main body. The oxygen concentrator of the present invention is provided with the oxygen concentrator main body 1 and the remote control device 6 to change the flow rate setting by remote control operation. The oxygen concentrator main body 1 adsorbs and removes nitrogen from the raw material air taken into it by pressure swing adsorption method and generates oxygen-enriched gas to supply it to the user at a predetermined flow rate. The user can change the supply flow rate of the oxygen-enriched gas by using the remote control device 6 even at a distance from the oxygen concentrator main body 1.

FIG. 2 shows the oxygen concentrator main body 1 and the respiratory disease patient or the user 3 inhaling the humidified oxygen-enriched gas. The pressure swing adsorption type oxygen concentrator main body 1 is provided with a HEPA filter 101 to remove fine dusts from the air which has passed through an air filter installed at the raw material air inlet port, an inlet air silencer 102, a compressor 103, a flow-path switching valve 104, an adsorption column 105, a check valve 107, a product tank 108, a pressure regulator valve 109, a flow rate setting means 110 and a particle filter 111. Thus, the oxygen-enriched gas can be generated by separating oxygen from the raw material air taken in from outside. In addition, the oxygen concentrator has a humidifier 201 to humidify the oxygen-enriched gas generated, a control means 401 to regulate the compressor and the flow-path switching valve 104 using the setting value of the flow rate setting means 110 and the measured values of an oxygen concentration sensor 301 and a flow rate sensor 302, a compressor box 501 to shield the noise generated by the compressor, and a cooling fan 502 to cool the compressor, which are built in its housing.

The raw material air is first taken in from outside through the air inlet port equipped with the outside air inlet filter 101 to remove foreign material such as dust and the inlet air silencer 102. Ordinary air contains about 21% of oxygen, 77% of nitrogen, 0.8% of argon, and 1.2% of other gases such as carbon dioxide. The apparatus of the present invention separates and yields the oxygen gas necessary as the respiratory gas.

The raw material air is pressurized with the compressor 103 and supplied to the adsorption column filled with the zeolite adsorbent, which preferentially adsorbs nitrogen over oxygen, the objective adsorption column being switched sequentially with the flow-path switching valve 104, yielding the unadsorbed oxygen from the adsorption column by selectively adsorbing and removing nitrogen contained in the air in about 77% in the adsorption column.

As the adsorption column, a single column or a multiple column composed of two or more columns formed with a cylinder type vessel filled with the adsorbent is usually used. Preferably, a multiple adsorption column is used in order to generate oxygen-enriched gas from the raw material air continuously and effectively. As the above-mentioned compressor, a swing type air compressor, as well as a revolving type air compressor such as a screw type, rotary type, scroll type or the like may be used. The power source of the motor to drive the compressor may be alternating current or direct current.

The oxygen-enriched gas containing oxygen as the major component, which was not adsorbed by the adsorption column 105, flows into the product tank 108 through the check valve 107 disposed to prevent the reverse flow into the adsorption column.

In order to adsorb nitrogen gas continuously from the raw material air freshly introduced, nitrogen adsorbed should be desorbed and removed from the adsorbent. For this purpose, the adsorbent is regenerated by switching the adsorbent column from the pressurized state which is realized by the compressor to the atmospheric or depressurized sate by opening and closing control of the flow-path switching valve, desorbing the nitrogen gas adsorbed under the pressurized state. In order to enhance the desorption efficiency in the desorption step, purging may be performed by connecting the product end of one adsorption column in the adsorption step with the other adsorption column in the desorption step among the two columns in series. Otherwise, the oxygen-enriched gas may be reversed into the adsorption column in the desorption step from the product tank as the purge gas. Usually, upon desorption of nitrogen, the adsorption column is vacuumed to atmospheric pressure from the maximum pressure state at one time, expelling nitrogen and the like adsorbed to outside. Since a loud airflow noise occurs at this time, a nitrogen exhaust silencer 503 is disposed at the outlet port.

The oxygen-enriched gas generated from the raw material air is stored in the product tank 108. The oxygen-enriched gas stored in the product tank contains oxygen in as high concentration as, for example, 90 to 95% and is supplied to the humidifier 201 with the supply flow rate and pressure regulated by the pressure regulator valve 109, the flow rate setting means 110, etc. Thus the humidified oxygen-enriched gas is supplied to the patient. As the humidifier, a humidifier which does not require water supply and supplies moisture taken in from outside air to the dry state oxygen-enriched gas with a module having a moisture permeating membrane such as Nafion and polyimide, as well as a bubbling type humidifier or a surface evaporation type humidifier which uses water as the moisture source, may be used.

As the flow rate setting means 110, a control valve may be used. Opening degree of the control valve may be controlled by the control means 401, which in turn is operated by the oxygen supply flow rate increase/decrease button 402 disposed in the oxygen concentrator main body, thus changing the flow rate to the predetermined value. In addition, besides the increase/decrease button 402 disposed in the oxygen concentrator main body, the control means 401 controls the control valve based on the flow rate setting signal transmitted from the remote control device 6 and received by the receiving means 403, which has a transmitting/receiving function, thus changing the oxygen supply flow rate to the predetermined value. Although the flow rate may be controlled independently by the remote control device and the oxygen concentrator main body, priority control and lock control, in which one of the setting change control is prohibited, may be possible as needed.

Supply flow rate to the adsorption column is controlled by detecting the setting value of the flow rate setting means 110 and controlling the revolving speed of the motor of the compressor 103 by the control means 401. If the setting flow rate is low, amount of the oxygen generation and the power consumption may be reduced by lowering the revolving speed.

Figure 3:
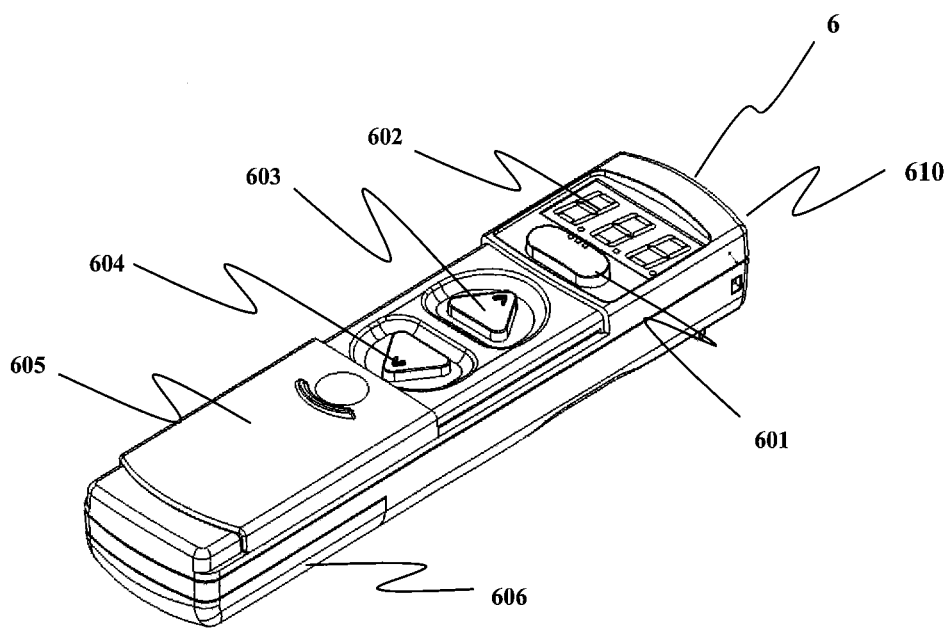
FIG. 3 is an external view of the remote control device as an embodiment of the oxygen concentrator of the present invention with a cover open.
Figure 4:
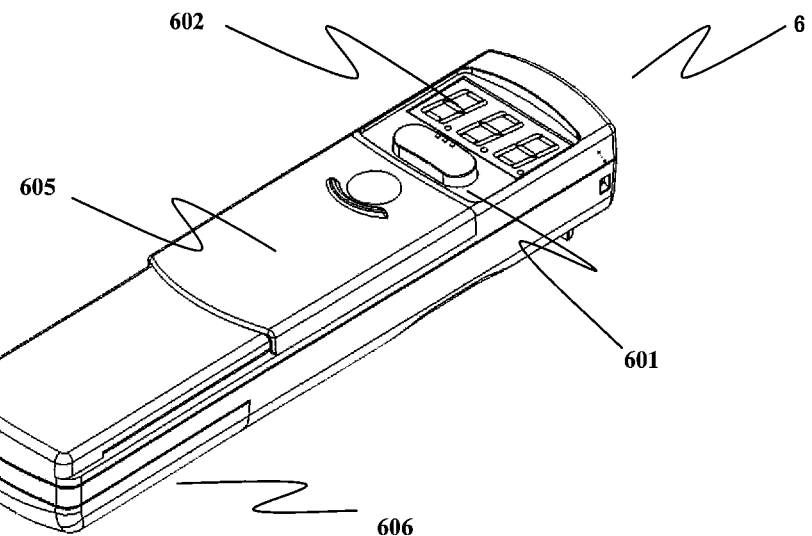
FIG. 4 is the remote control device with a cover closed.
Figure 5:
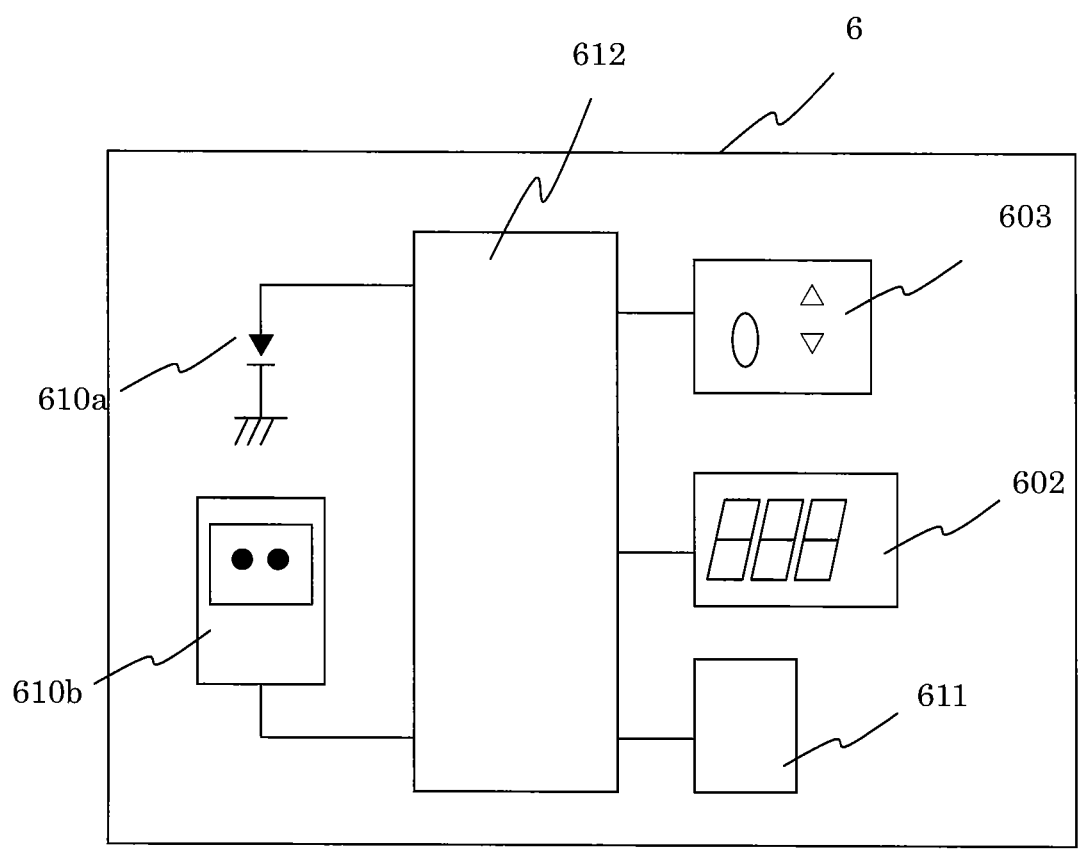
FIG. 5 is a block diagram of the communication system of the remote control device.
Figure 6:
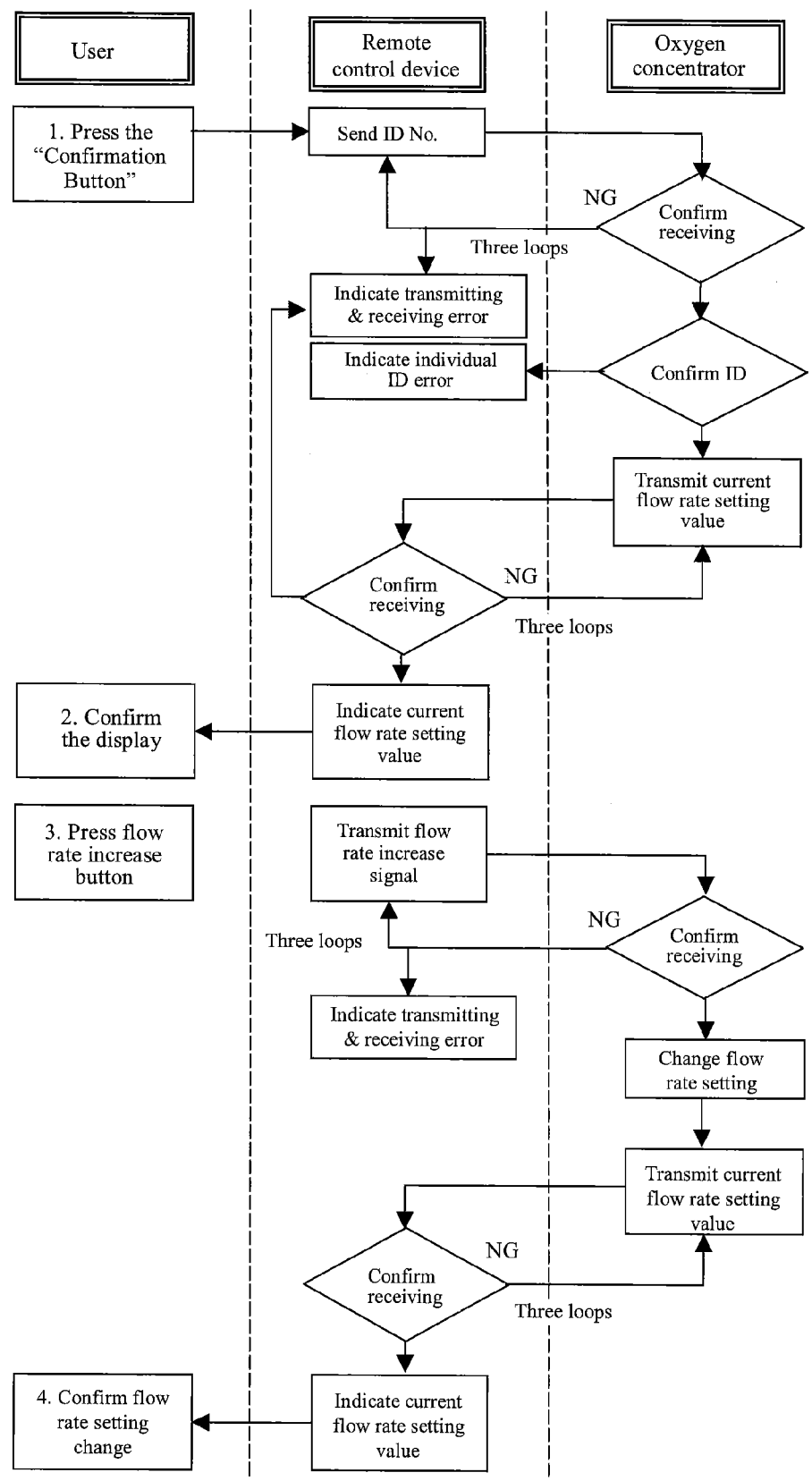
FIG. 6 shows the communication flow of remote control to change the supply flow rate of the oxygen-enriched gas of the oxygen concentrator main body 1 using the remote control device 6.

FIG. 3 and FIG. 4 show the remote control device 6 included in the pressure swing adsorption type oxygen concentrator which is an embodiment of the present invention. FIG. 5 is a block diagram of the communication system of the remote control device 6. FIG. 6 shows the communication flow of remote control to change the supply flow rate of the oxygen-enriched gas of the oxygen concentrator main body 1 using the remote control device 6.

The wireless transmitting/receiving part 610 of the remote control device 6 is located at the end part of the operating means. Bidirectional communication can be done by operating the remote control device with the transmitting/receiving part 610 pointing at the signal transmitting/receiving part 403 located at the front side of the oxygen concentrator main body. Infrared communication may be used due to its signal directivity. Bidirectional communication is performed by disposing an infrared emitter 610a and an infrared detector 610b at the transmitting/receiving part 610 of the remote control device, as well as an infrared emitter and an infrared detector at the transmitting/receiving part 403 of the oxygen concentrator main body.

When the user transfers from resting mode to exerting mode or when the user feels difficulty in breathing during oxygen inhalation, the patient presses the confirmation button 601 on the remote control device 6. The remote control device 6 thereby transmits a signal to confirm the individual ID toward the oxygen concentrator main body 1. Thus, a combination of the patient who operates the remote control device and the oxygen concentrator which is used by the patient can be distinguished on a one-to-one basis, even when a plurality of the oxygen concentrators of the present invention are used at a medical facility such as a hospital. If the individual IDs coincide at the oxygen concentrator main body 1 which has received the signal transmitted by the remote control device 6, the flow rate setting value of the running oxygen concentrator main body 1 is returned to the remote control device 6.

If a communication error has occurred during this transmitting/receiving process, communication may be secured by repeating transmitting/receiving at least three times. In case that the return signal of the flow rate setting value cannot be received even though the individual ID has been transmitted by the remote control device due to the communication error, the display 602 on the remote control device 6 indicates that the communication error has occurred.

In case that the transmitting/receiving has succeeded, the display 602 indicates the current flow rate setting value. After confirming this, the patient selects increasing or decreasing of the flow rate setting and presses the button 603 or 604, respectively. The remote control device 6 transmits the signal for increasing or decreasing the flow rate setting to the oxygen concentrator main body 1, which in turn changes the flow rate setting based on the signal. In case that the change of the flow rate setting has succeeded, the oxygen concentrator 1 transmits the flow rate setting value after the change to the remote control device 6 and the display 602 indicates the value. In case that the return signal of the flow rate setting value after the change has not been received due to the communication error although the remote control device 6 has transmitted the signal for changing the flow rate setting, the display 602 on the remote control device 6 indicates that the communication error has occurred. A sound signal from the buzzer 611 in combination with the display, such as a short beep sound in case that the communication has succeeded and a long or continuous sound in case that the communication error has occurred, may allow more reliable confirmation of the communication state.

In the case of a remote control device used for general electric appliances, setting can be changed by a single operation of transmitting the information on the value to be changed, which has been predetermined on the remote control device, to the main body. However, since the oxygen concentrator of the present invention is used for oxygen inhalation therapy in which the supply flow rate is determined according to the physician's prescription and directly influences the therapeutic effect, the flow rate setting must be changed very carefully. In the method of the present invention, the flow rate is increased or decreased stepwise in association with confirmation of the flow rate indication in order to secure the difference between the flow rate to be changed and the actual supply flow rate to the minimum, considering the safety in case that the patient is not aware of the communication error between the remote control device and the oxygen concentrator main body.

The flow rate setting of the oxygen concentrator may also be changed at the oxygen concentrator main body. Therefore, if the patient changes the flow rate based on the previous flow rate setting value stored in the remote control device, there is a risk of the prescription change by the patient's own mistake and a possibility of failure in demanded oxygen supply. In addition, sudden setting change from low flow rate value to high flow rate value may cause a disadvantage of greater load on the device in the case of the apparatus with a large oxygen generation capacity such as 5 L/min or 10 L/min. Therefore, when the flow rate setting is changed at the remote control device of the oxygen concentrator in the present invention, the flow rate of the oxygen-enriched gas supplied from the current oxygen concentrator main body is confirmed without exception and the flow rate is changed stepwise by the increase/decrease buttons 603 and 604 for each of the flow rate setting predetermined by the device, for example, for every 0.5 L/min or every 1 L/min, based on the confirmed flow rate value. The control means B612 controls so that the flow rate cannot be changed to the next step unless the flow rate value after the change is returned to the remote control device from the oxygen concentrator main body.

In the remote control device 6 included in the oxygen concentrator of the present invention, the lighting time of the display 602 is set to 10 seconds and the operation thereafter is not allowed in order to reduce consumption of the battery. If desired, the flow rate setting may be changed by pressing the confirmation button 601 and restarting the remote control device 6.

Although a wireless communication is used to transmit and receive the signal in the present invention, the present technique may also be applied to the wired remote control device. Infrared ray and radio wave may be used as the wireless method. In order to prevent operational error, infrared ray is preferably used because the remote control device 6 should be operated facing to the oxygen concentrator 1 from the front due to the directivity of the wireless signal. This allows the remote control operation watching the display of the flow rate setting on the oxygen concentrator main body, providing an improvement of safety because, for example, the displays of both of the remote control device and the oxygen concentrator main body may be confirmed.

In addition, the button has a cover 605 to prevent operational error due to the unnecessary button pressing during sleeping or by child's mischief in the present invention. Although the present embodiment discloses a slide type cover, other type of cover such as a door type cover may be used. In addition, the operation buttons of the remote control device, especially the flow rate setting change buttons 603 and 604 are located on a surface lower than the housing surface of the remote control device 6, so that the operation button cannot be pressed even if the remote control device is mistakenly laid under the user's body during sleep.

INDUSTRIAL APPLICABILITY

The oxygen concentrator of the present invention is used as a therapeutic oxygen concentrator or an oxygen source for the oxygen inhalation therapy to the patients suffering from respiratory diseases such as asthma, pulmonary emphysema, chronic bronchitis, etc. Furthermore, the remote control device characterizing the present invention allows a secure operation of changing the flow rate setting at hand of the patient. The patient can also be aware of the communication error in case that has occurred and can try the communication again. Therefore, the oxygen concentrator of the present invention may be utilized as the convenient and safe oxygen concentrator.

The invention claimed is:

1. An oxygen concentrator which allows the flow rate setting value of the oxygen-enriched gas to be changed by remote control operation, comprising an oxygen concentrator main body provided with a flow rate setting means to separate oxygen in air and supply the oxygen-enriched gas generated at a predetermined flow rate and a remote control device to control the oxygen concentrator main body from a distance, the oxygen concentrator main body comprising a communication means to transmit and receive the information on the flow rate setting value to and from the remote control device and a control means A to confirm the information and control the flow rate setting, the remote control device comprising a confirmation button to confirm the flow rate setting value of the oxygen-enriched gas currently supplied by the oxygen concentrator main body, a flow rate setting change button to change the flow rate setting value of the oxygen-enriched gas supplied by the oxygen concentrator main body, a display to indicate the flow rate setting value, and a communication means to transmit and receive the information on the flow rate setting value to and from the oxygen concentrator main body, and the remote control device further comprising a control means B which does not allow the operation of the flow rate setting change button unless the remote control device receives the information on the flow rate setting value of the oxygen-enriched gas supplied by the current oxygen concentrator main body.

2. The oxygen concentrator according to claim 1, wherein the flow rate setting change button of the remote control device is a button to change the flow rate setting value in a stepwise fashion and the control means B is a means to transmit the flow rate setting information after a change of the first stage to the oxygen concentrator main body and to control so that the operation of the flow rate setting change button to change the flow rate to the next stage is not allowed unless the remote control device receives the information on the flow rate setting value of the oxygen-enriched gas supplied by the oxygen concentrator main body after the change.

3. The oxygen concentrator according to claim 1, wherein the oxygen concentrator main body and the remote control device are each provided with individual ID, the remote control device transmitting its ID to the oxygen concentrator main body when the confirmation button is pressed, the oxygen concentrator main body returning the information on the flow rate setting value of the oxygen-enriched gas supplied by the current oxygen concentrator main body if the ID information received and the ID of the oxygen concentrator main body coincide and transmitting an error message if the IDs do not coincide.

4. The oxygen concentrator according to claim 1, wherein the remote control device has a display function to indicate the error message at the display and a buzzer to sound an alarm when an error has occurred in the communication between the remote control device and the oxygen concentrator main body.

5. The oxygen concentrator according to claim 1, wherein the communication means between the remote control device and the oxygen concentrator main body is an infrared data communication means.

6. The oxygen concentrator according to claim 1, wherein the flow rate setting change button of the remote control device is disposed on a surface lower than the housing surface of the remote control device, so that the button surface is located lower than the housing surface.

\* \* \* \* \*